(12) United States Patent
Iliev et al.

(10) Patent No.: US 11,864,897 B2
(45) Date of Patent: Jan. 9, 2024

(54) SYSTEMS AND METHODS FOR CLASSIFYING USER TASKS AS BEING SYSTEM 1 TASKS OR SYSTEM 2 TASKS

(71) Applicant: TOYOTA RESEARCH INSTITUTE, INC., Los Altos, CA (US)

(72) Inventors: Rumen Iliev, Millbrae, CA (US); Kent Lyons, Los Altos, CA (US); Charlene C. Wu, San Francisco, CA (US); Matthew Lee, Mountain View, CA (US); Yanxia Zhang, Foster City, CA (US); Yue Weng, San Mateo, CA (US)

(73) Assignee: Toyota Research Institute, Inc., Los Altos, CA (US)

( * ) Notice: Subject to any disclaimer, the term of this patent is extended or adjusted under 35 U.S.C. 154(b) by 312 days.

(21) Appl. No.: 17/227,671

(22) Filed: Apr. 12, 2021

(65) Prior Publication Data
US 2022/0322986 A1 Oct. 13, 2022

(51) Int. Cl.
*A61B 5/16* (2006.01)
*G06N 20/00* (2019.01)
(Continued)

(52) U.S. Cl.
CPC ............ *A61B 5/165* (2013.01); *A61B 5/0205* (2013.01); *A61B 5/163* (2017.08); *G06N 20/00* (2019.01);
(Continued)

(58) Field of Classification Search
CPC ....... A61B 5/165; A61B 5/0205; A61B 5/163; A61B 5/024; G06N 20/00
See application file for complete search history.

(56) References Cited

U.S. PATENT DOCUMENTS 7,580,742 B2 8/2009 Tan et al.
10,068,490 B2 9/2018 Hibbs et al.
(Continued)

FOREIGN PATENT DOCUMENTS

CN 110069325 B 12/2020
JP 3976035 B2 * 9/2007
(Continued)

OTHER PUBLICATIONS

Norman et al., "The Etiology of Diagnostic Errors:A Controlled Trial of System 1 VersusSystem 2 Reasoning" Academic medicne, vol. 89 No. 2 (2014):277-284, Feb. 2014.*
(Continued)

*Primary Examiner* — Christopher A Flory
(74) *Attorney, Agent, or Firm* — Dinsmore & Shohl LLP (57) ABSTRACT

Systems and methods for determining whether a user employs System 1 type thinking or System 2 type thinking when engaged in a task are disclosed. The systems and methods include determining one or more properties of the task based on information regarding the task received from a database storing information regarding the task, determining one or more properties of the user with respect to the task, determining a state of the user based on one or more physiological sensors configured to sense one or more characteristics of the user, and determining that the user employs System 1 type thinking or System 2 type thinking when engaged in the task based on the determined one or more properties of the task, the determined one or more properties of the user, and the determined state of the user.

18 Claims, 5 Drawing Sheets

(51) Int. Cl.
  *A61B 5/0205* (2006.01)
  *A61B 5/024* (2006.01)
  *G06F 16/245* (2019.01)
  *A61B 5/00* (2006.01)

(52) U.S. Cl.
  CPC ............. *A61B 5/024* (2013.01); *A61B 5/4266* (2013.01); *A61B 5/6893* (2013.01); *G06F 16/245* (2019.01)

(56) References Cited

U.S. PATENT DOCUMENTS

| | | | | |
|---|---|---|---|---|
| 2009/0319459 | A1* | 12/2009 | Breazeal | G06N 3/004 901/1 |
| 2011/0105925 | A1* | 5/2011 | Hatakeyama | A61B 5/16 600/509 |
| 2014/0344718 | A1* | 11/2014 | Rapaport | H04L 51/52 715/753 |
| 2020/0008725 | A1* | 1/2020 | Bach | A61B 5/369 |
| 2020/0225054 | A1* | 7/2020 | Ramtirth | A61B 5/0022 |
| 2020/0247420 | A1* | 8/2020 | Gunaratne | G05D 1/0055 |
| 2021/0339759 | A1* | 11/2021 | Fouad | B60W 60/0051 |

FOREIGN PATENT DOCUMENTS

| | | |
|---|---|---|
| JP | 2019067392 A | 4/2019 |
| WO | 2019184231 A1 | 10/2019 |

OTHER PUBLICATIONS

Norman et al., "The Etiology of Diagnostic Errors: A Controlled Trial of System 1 Versus System 2 Reasoning." Academic Medicine, vol. 89, No. 2 (2014): 277-284, Feb. 2014.

Bago et al., "The Smart System 1: Evidence for the Intuitive Nature of Correct Responding on the Bat-And-Ball Problem." Thinking & Reasoning 25, No. 3 (2019): 257-299. URL: https://www.tandfonline.com/doi/pdf/10.1080/13546783.2018.1507949?casa_token=JFfUC2U7kK4AAAAA: Tw74tX2lzXiut38twVMNKxnr4dvyKX6hvhFCTxBKDz-azmFfJGsLX_Yh-dB2MDZnZ_mSiYXIJUZT8A, Feb. 14, 2019.

Milkman et al., "How Can Decision Making Be Improved?." (2008). URL: https://citeseerx.ist.psu.edu/viewdoc/download?doi=10.1.1.334.8907&rep=rep1&type=pdf, 2008.

* cited by examiner

SYSTEMS AND METHODS FOR CLASSIFYING USER TASKS AS BEING SYSTEM 1 TASKS OR SYSTEM 2 TASKS

TECHNICAL FIELD

The present specification generally relates to systems and methods for determining whether a user employs System 1 type thinking or System 2 type thinking when engaged in a task.

BACKGROUND

Studies on human reasoning suggest that a large part of human reasoning capabilities can be approximated by a dual-process model distinguishing between rapid, automatic intuitions and slower, deliberate analytical processing. These two are typically referred to as System 1 type thinking and System 2 type thinking, respectively. In general, System 2 type thinking has a cognitive advantage in terms of accuracy and generalizability, and System 1 type thinking has the advantage in terms of speed and cognitive processing cost in terms of working memory and attention. Distinguishing between System 1 type thinking and System 2 type thinking enable human interactive systems to be tailored to communicate with a user in a more effective manner.

Accordingly, there is a need for systems and methods for determining whether a user employs System 1 type thinking or System 2 type thinking when engaged in a task.

SUMMARY

In embodiments, a method for determining whether a user employs System 1 type thinking or System 2 type thinking when engaged in a task is disclosed. The method includes determining one or more properties of the task based on information regarding the task received from a database storing information regarding the task, determining one or more properties of the user with respect to the task, determining a state of the user based on one or more physiological sensors configured to sense one or more characteristics of the user, and determining that the user employs System 1 type thinking or System 2 type thinking when engaged in the task based on the determined one or more properties of the task, the determined one or more properties of the user, and the determined state of the user.

In some embodiments, a system for determining whether a user employs System 1 type thinking or System 2 type thinking when engaged in a task is disclosed. The system includes one or more physiological sensors configured to sense one or more characteristics of the user, and an electronic control unit communicatively coupled to the one or more physiological sensors. The electronic control unit configured to determine one or more properties of the task based on information regarding the task received from a database storing information regarding the task, determining one or more properties of the user with respect to the task, determining a state of the user based on the one or more characteristics of the user sensed by the one or more physiological sensors, and determine that the user employs System 1 type thinking or System 2 type thinking when engaged in the task based on the determined one or more properties of the task, the determined one or more properties of the user, and the determined state of the user.

In some embodiments, a system for predicting whether a user employs System 1 type thinking or System 2 type thinking when engaged in a task is disclosed. The system includes one or more physiological sensors configured to sense one or more characteristics of the user, and an electronic control unit communicatively coupled to the one or more physiological sensors. The electronic control unit configured to implement a machine learning model, receive, as an input to the machine learning model, one or more properties of the task, one or more properties of the user with respect to the task, and a state of the user based on the one or more characteristics of the user sensed by the one or more physiological sensors, and predict, with the machine learning model, that the user employs System 1 type thinking or System 2 type thinking when engaged in the task based on the one or more properties of the task, the one or more properties of the user, and the state of the user.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Embodiments described herein relate to systems and methods for determining whether a user employs System 1 type thinking or System 2 type thinking when engaged in a task. System 1 type thinking refers to the thought process where a user utilizes automatic, intuitive, and unconscious thinking. That is, System 1 type thinking generally requires little energy or attention. However, when a user employs System 1 type thinking, responses can be biased prone since there is little to no analytical reasoning employed. Additionally, System 1 type thinking continuously creates impressions, intuitions, and judgments based on our daily routines. That is, when faced with a decision, humans automatically employ System 1 type thinking. Accordingly, System 1 type thinking is influential and can guide most day-to-day decisions. However, unlike System 1 type thinking, System 2 type thinking requires energy and attention to think through choices and information. System 2 type thinking filters out automatic instincts and biases to make an informed and/or reasoned choice. That is, System 2 type thinking is a slow, controlled, and analytical method of thinking where reason dominates. Furthermore, System 2 type thinking typically occurs when a user is faced with a new situation or when the user makes a conscious effort to engage in the details of a task.

However, determining whether a user employs System 1 type thinking or System 2 type thinking when engaged in a task is not solely based on the particularities of the task itself. A determination, as described in more detail herein, involves the particularities of the user who is performing the particular task. For example, an inexperienced user may utilize System 2 type thinking for a particular task, whereas an experienced user, performing the same task, may utilize System 1 type thinking.

The present embodiments disclose systems and methods configured to collect and analyze information from at least three particular categories to determine whether a user is or will use either System 1 type thinking or System 2 type thinking for the particular task. The three factors include properties of the task, properties of the user, and the state of the user. As described in more detail herein, analysis of information pertaining to the three factors is carried out by a computing device such as an electronic control unit. The electronic control unit is configured to receive sensor data from one or more sensors as well as information from one or more data storage devices such as a database pertaining to one or more of the three factors. The electronic control unit analyzes the data and information using one or more algorithms and/or a machine learning model as described in more detail herein.

In some embodiments, the systems and methods described herein may be implemented to enhance or improve interaction and/or communication between a system deploying a task such as a navigation system of a vehicle configured to provide navigation information and the user. For example, as described in more detail herein, once it is determined that a user is either employing System 1 type thinking or System 2 type thinking, the vehicle system such as the navigation system or another vehicle or non-vehicle based system may be configured to employ a system and method of interaction and/or communication consistent with the type of thinking a user is employing for the task.

The following will now describe these systems and methods in more detail with reference to the drawings and where like numbers refer to like structures.

Figure 1:
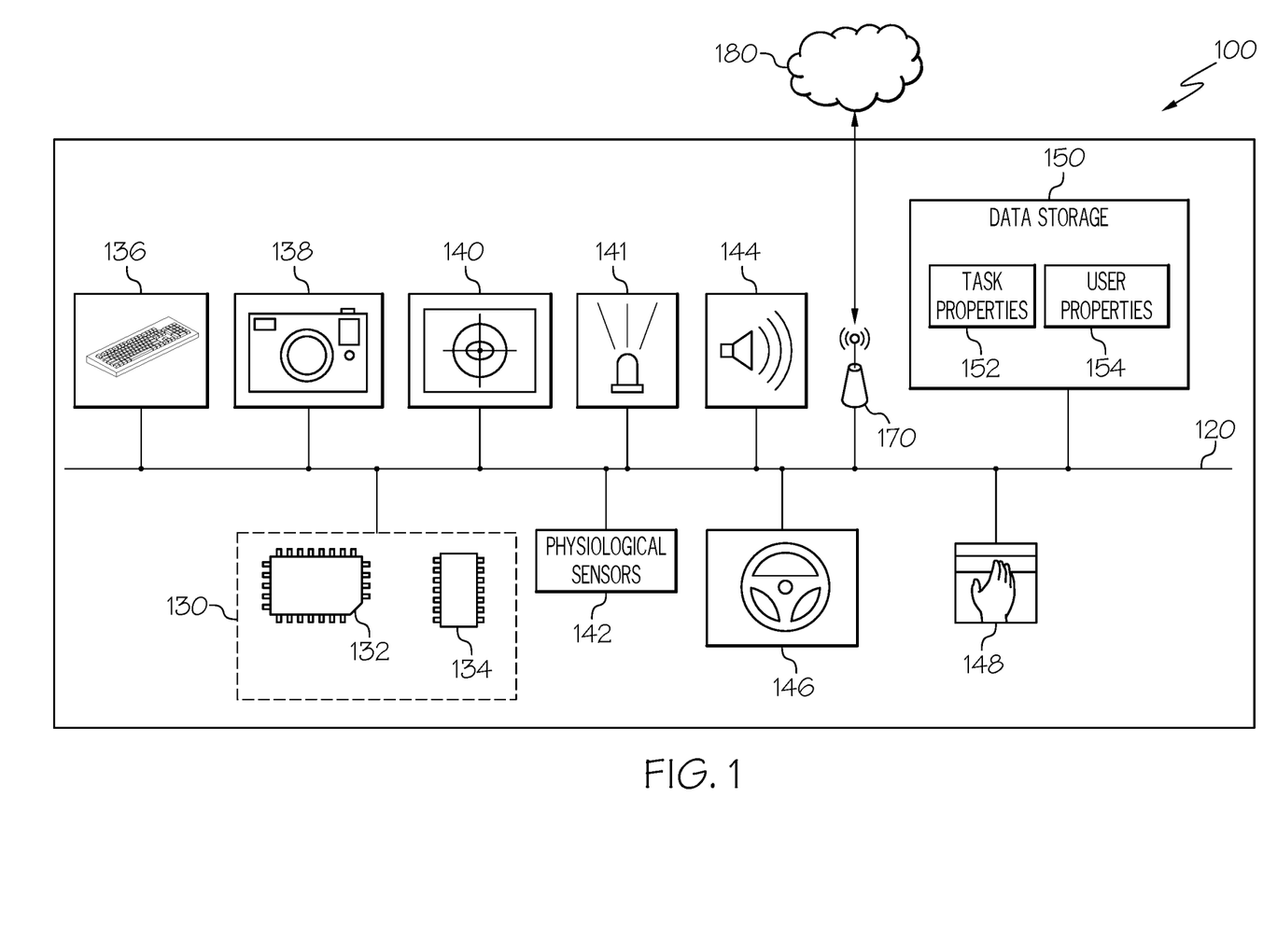
FIG. 1 depicts an illustrative system for predicting or determining whether a user employs System 1 type thinking or System 2 type thinking when engaged in a task, according to one or more embodiments shown and described herein.

Referring now to FIG. 1, a system 100 for determining whether a user employs System 1 type thinking or System 2 type thinking when engaged in a task is depicted. The system 100 includes an electronic control unit 130. The electronic control unit 130 includes a processor 132 and a memory component 134. The system 100 also includes a communication bus 120, one or more input devices 136, one or more cameras 138, an eye-tracking system 140, an illuminating device 141, one or more physiological sensors 142, a speaker 144, a steering wheel system 146, a display 148, a data storage component 150, and/or network interface hardware 170. The system 100 may be communicatively coupled to a network 180 by way of the network interface hardware 170. The components of the system 100 are communicatively coupled to each other via the communication bus 120.

It is understood that the embodiments depicted and described herein are not limited to the components or configurations depicted and described with respect to FIG. 1, rather FIG. 1 is merely for illustration. The various components of the system 100 and the interaction thereof will be described in detail herein.

The communication bus 120 may be formed from any medium that is capable of transmitting a signal such as, for example, conductive wires, conductive traces, optical waveguides, or the like. The communication bus 120 may also refer to the expanse in which electromagnetic radiation and their corresponding electromagnetic waves traverses. Moreover, the communication bus 120 may be formed from a combination of mediums capable of transmitting signals. In one embodiment, the communication bus 120 comprises a combination of conductive traces, conductive wires, connectors, and buses that cooperate to permit the transmission of electrical data signals to components such as processors 132, memories, sensors, input devices, output devices, and communication devices. Accordingly, the communication bus 120 may comprise a bus. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium. The communication bus 120 communicatively couples the various components of the system 100. As used herein, the term "communicatively coupled" means that coupled components are capable of exchanging signals with one another such as, for example, electrical signals via conductive medium, electromagnetic signals via air, optical signals via optical waveguides, and the like.

The electronic control unit 130 may be any device or combination of components comprising a processor 132 and the memory component 134. The processor 132 of the system 100 may be any device capable of executing the machine-readable instruction set stored in the memory component 134. Accordingly, the processor 132 may be an electric controller, an integrated circuit, a microchip, a field programmable gate array, a computer, or any other computing device. The processor 132 is communicatively coupled to the other components of the system 100 by the communication bus 120. Accordingly, the communication bus 120 may communicatively couple any number of processors 132 with one another, and allow the components coupled to the communication bus 120 to operate in a distributed computing environment. Specifically, each of the components may operate as a node that may send and/or receive data. While the embodiment depicted in FIG. 1 includes a single processor 132, other embodiments may include more than one processor 132.

The memory component 134 of the system 100 is coupled to the communication bus 120 and communicatively coupled to the processor 132. The memory component 134 may be a non-transitory computer readable memory implemented as, for example, RAM, ROM, flash memories, hard drives, or any non-transitory memory device capable of storing machine-readable instructions such that the machine-readable instructions can be accessed and executed by the processor 132. The machine-readable instruction set may comprise logic or algorithm(s) written in any programming language of any generation (e.g., 1GL, 2GL, 3GL, 4GL, or 5GL) such as machine language that may be directly executed by the processor 132, or assembly language, object-oriented programming (OOP), scripting languages, microcode, etc., that may be compiled or assembled into machine readable instructions and stored in the memory component 134. Alternatively, the machine-readable instruction set may be written in a hardware description language (HDL), such as logic implemented via either a field-programmable gate array (FPGA) configuration or an application-specific integrated circuit (ASIC), or their equivalents. Accordingly, the functionality described herein may be implemented in any conventional computer programming language, as pre-programmed hardware elements, or as a combination of hardware and software components. While the system 100 depicted in FIG. 1 includes a single memory component 134, other embodiments may include more than one memory component 134.

The system 100 includes one or more input devices 136. The one or more input devices 136 may be any device configured to enable a user to input information into the system. For example, the one or more input devices 136 may include a keyboard, mouse, stylus, a scanner, a gesture camera, microphone, or the like. The system 100 may also include one or more cameras 138. The one or more cameras 138 may be communicatively coupled to the communication bus 120 and to the processor 132. The one or more cameras 138 may be any device having an array of sensing devices (e.g., pixels) capable of detecting radiation in an ultraviolet wavelength band, a visible light wavelength band, or an infrared wavelength band. The one or more cameras 138 may have any resolution. The one or more cameras 138 may be an omni-directional camera, or a panoramic camera, for example. In some embodiments, one or more optical components, such as a mirror, fish-eye lens, or any other type of lens may be optically coupled to each of the one or more cameras 138. The one or more cameras 138 may capture image data or video data of an environment of a vehicle.

In some embodiments, the system 100 may be implemented in a vehicle 110 (FIG. 3) to enhance a driver's interaction and/or communication with one or more vehicle systems. For example, as described in more detail herein, once it is determined that a user is either employing system 1 or system 2 type thinking, a vehicle system or another system may be configured to employ a system and method of interaction and/or communication consistent with the type of thinking a user is employing for the task. For example, the one or more cameras 138 may be implemented by the system 100 to capture events occurring in the environment around the driver to provide information pertaining to the state of the user and/or the properties of the task.

The system 100 may include an eye-tracking system 140 for tracking eye movement and/or gaze of a subject. The eye-tracking system 140 may include one or more cameras 138 and/or an array of infrared light detectors positioned to view one or more eyes of a subject. The eye-tracking system 140 may also include or be communicatively coupled to an illuminating device 141 which may be an infrared or near-infrared light emitter. The illuminating device 141 may emit infrared or near-infrared light, which may be reflected off a portion of the eye creating a profile that is more readily detectable than visible light reflections off an eye for eye-tracking purposes. In some embodiments, the eye-tracking system 140 may also be configured to determine pupil dilation or constriction of a user's eyes.

The eye-tracking system 140 may be spatially oriented in an environment and generate a gaze direction vector. One of a variety of coordinate systems may be implemented such as user coordinate system (UCS). For example, the UCS has its origin at the center of the front surface of the gaze-tracker. With the origin defined at the center of the front surface (e.g., the eye-tracking camera lens) of the eye-tracking system 140, the gaze direction vector may be defined with respect to the location of the origin. Furthermore, when spatially orienting the eye-tracking system 140 in the environment, all other objects including the one or more cameras 138 may be localized with respect to the location of the origin of the eye-tracking system 140. In some embodiments, an origin of the coordinate system may be defined at a location on the subject, for example, at a spot between the eyes of the subject. Irrespective of the location of the origin for the coordinate system, a calibration process may be employed by the eye-tracking system 140 to calibrate a coordinate system for collecting eye-tracking data, pupil dilation data, and/or eye movement information that may be used to determine the state of the user, properties of the task, and/or properties of the user.

Still referring to FIG. 1, the system 100 may further include one or more physiological sensors 142. The one or more physiological sensors 142 may be communicatively coupled to the communication bus 120 and to the electronic control unit 130. The one or more physiological sensors 142 may be any device capable of monitoring and capturing physiological states of the human body, such as a driver's stress level through monitoring electrical activity of the heart, skin conductance, respiration, or the like. The one or more physiological sensors 142 include sensors configured to measure bodily events such as heart rate change, electrodermal activity (EDA), muscle tension, and cardiac output. The one or more physiological sensors 142 may monitor brain waves through electroencephalography, EEG, electrodermal activity through a skin conductance response, SCR, and galvanic skin response, GSR, cardiovascular measures such as heart rate, HR; beats per minute, BPM; heart rate variability, HRV; vasomotor activity, muscle activity through electromyography, EMG, changes in pupil diameter with thought and emotion through pupillometry (e.g., pupillometry data), eye movements, recorded via the electrooculogram, EOG and direction-of-gaze methods, and cardiodynamics recorded via impedance cardiography, or other physiological measures.

The physiological sensors 142 may generate physiological response data that may be utilized to train or evolve a neural network 400 to determine a state of a user. Physiological response data of a subject can be indicative of a state of the user. For example, the physiological sensors 142 may be able to detect characteristics of a user that are indicative of the user's stress level, fatigue level, and/or state of health. In some instances, the physiological response data can indicate whether a user is multitasking or the user is focused on a particular task. For example, physiological response data that indicates rapid heartbeat, dilated pupils, rapid movement of the eyes, and/or the presence of sweat can be indicative of a user having an elevated stress level. By way of another example, physiological response data that indicates sluggish eye movement and/or presence of discoloration of or around the eyes can be indicative of a user being fatigued. Moreover, physiological response data pertaining to a user's body temperature, blood oxygen levels, heart rate (e.g., an active or resting heart rate), blood pressure, respiration rate, oxygen saturation levels, or the like are indicative of the state of health of the user.

The system 100 may also include a speaker 144. The speaker 144 (i.e., an audio output device) is coupled to the communication bus 120 and communicatively coupled to the electronic control unit 130. The speaker 144 transforms audio message data as signals from the processor 132 of the electronic control unit 130 into mechanical vibrations producing sound. For example, the speaker 144 may provide information to a user in audible form. Audible information may be used independently or in combination with visual imagery, textual data or the like. However, it should be understood that, in other embodiments, the system 100 may not include the speaker 144.

The steering wheel system 146 is coupled to the communication bus 120 and communicatively coupled to the electronic control unit 130. The steering wheel system 146 may comprise a plurality of sensors such as physiological sensors 142 located in the steering wheel. Additionally, the steering wheel system 146 may include motors or components to provide haptic feedback to the driver. For example, the steering wheel system 146 may be configured to provide vibrations of varying intensity through the steering wheel as a means of communicating or alerting the driver.

The system 100 may include a display 148 for presenting information in a visual format to a user. The display 148 may be a heads-up display system, a navigation display, a smartphone or computing device, a television, or the like. The display 148 may include any medium capable of transmitting an optical output such as, for example, a cathode ray tube, light emitting diodes, a liquid crystal display, a plasma display, or the like. The display 148 may also include one or more input devices. The one or more input devices may be any device capable of transforming user contact into a data signal that can be transmitted over the communication bus 120 such as, for example, a button, a switch, a knob, a microphone or the like. In some embodiments, the one or more input devices include a power button, a volume button, an activation button, a scroll button, or the like. The one or more input devices may be provided so that the user may interact with the display 148, such as to navigate menus, make selections, set preferences, and other functionality described herein. In some embodiments, the input device includes a pressure sensor, a touch-sensitive region, a pressure strip, or the like.

A data storage component 150 that is communicatively coupled to the system 100 may be a volatile and/or non-volatile digital storage component and, as such, may include random access memory (including SRAM, DRAM, and/or other types of random access memory), flash memory, registers, compact discs (CD), digital versatile discs (DVD), and/or other types of storage components. The data storage component 150 may reside local to and/or remote from the system 100 and may be configured to store one or more pieces of data such as one or more properties of one or more tasks 152, one or more properties of one or more users 154, and the like.

The one or more properties of one or more tasks 152 may include properties such as the type of task. Types of tasks may include an incidental task, a routine task, a project, a reactionary task, a problem-solving task, a decision-making task, a planning task, a collaborative or independent task, a creative task, or the like. Each type of task may be categorized as a task that involves System 1 type thinking or System 2 type thinking. However, the type of task alone may not indicative of the type of thinking that a user implements. Other properties such as the typical length it takes to complete the task, the number of steps involved with completing the task, what senses such as sight, hearing taste, or touch are involved with completing the task, and/or if the task involves the processing or words, written information, sounds, and/or images may be considered in determining whether the one or more properties of the task are indicative of a task that a user employs System 1 or System 2 type thinking. For example, tasks that have few steps, tasks that can be completed in a short period of time, tasks that involve the processing of visual and/or audible information or the like generally cause the user to engage in System 1 type thinking. On the other hand, for example, tasks that have more steps, take several minutes or hours to complete, involve the processing of words and/or written information or the like generally cause the user to engage in System 2 type thinking. Accordingly, by analyzing one or more properties of a task, the system and method can determine whether the properties of the task are indicative of a task that involves System 1 type thinking or System 2 type thinking. As described in more detail herein, the determination that a user is employing System 1 type thinking or System 2 type thinking for a particular task based on the one or more properties of the task may be a binary determination (e.g., either System 1 type thinking or System 2 type thinking) or a prediction defined by a likelihood that the user is employing System 1 type thinking or System 2 type thinking.

The one or more properties of the one or more users 154 may include properties such as experience level of the user performing the task, the number of times the user has completed the particular task or similar tasks in the past, the amount of time that the user previously engaged in solving the same or similar task, whether the user is proficient in a set of particular skills that correlate to the one or more properties of the task, the frequency in which a user interacts with the particular task and/or the like. The one or more properties of the one or more users 154 may be stored as user profiles in the data storage component 150 and/or the memory component 134 of the electronic control unit 130. The user profiles may be developed based on past interactions a user had with the system in completing a task. For example, the system may learn from previous iterations how a user solves the task, whether they can complete the task in a timely or efficient manner, or the like. In some embodiments, a user profile may be developed independently of past interactions with a task. For example, the system may prompt a user to complete a survey that collects information directly provided by a user such as their education level or skills, a prompt that evaluates a user's set of skills through questions or simple cognitive tasks, a prompt that obtains a user's comfort level with specific types of tasks through a rating process, or the like. The process of gathering information about a user may be coupled with monitoring a user's physiological states to determine, for example, whether a user is stressed when faced with a particular category of tasks or subject matter. Such information is indicative, in part, as to what type of thinking a user employs when handling a particular task.

For example, a user that is experienced in solving or completing a particular task may not exhibit an elevated level of stress unlike someone who is new to the particular task. Moreover, a user that is experienced with a particular task is more likely to utilize System 1 type thinking as opposed to someone who is new to the particular task who is likely to utilize System 2 type thinking. As described in more detail herein, the determination that a user is employing System 1 type thinking or System 2 type thinking for a particular task based on the one or more properties of the one or more users may be a binary determination (e.g., either System 1 type thinking or System 2 type thinking) or a prediction defined by a likelihood that the user is employing System 1 type thinking or System 2 type thinking.

Still referring to FIG. 1, the system 100 may also include network interface hardware 170 that is communicatively coupled to the electronic control unit 130 via the communication bus 120. The network interface hardware 170 may include any wired or wireless networking hardware, such as a modem, LAN port, Wi-Fi card, WiMax card, mobile communications hardware, and/or other hardware for communicating with a network 180 and/or other devices and systems. For example, the system 100 may be communicatively coupled to a network 180 by way of the network interface hardware 170.

Figure 2:
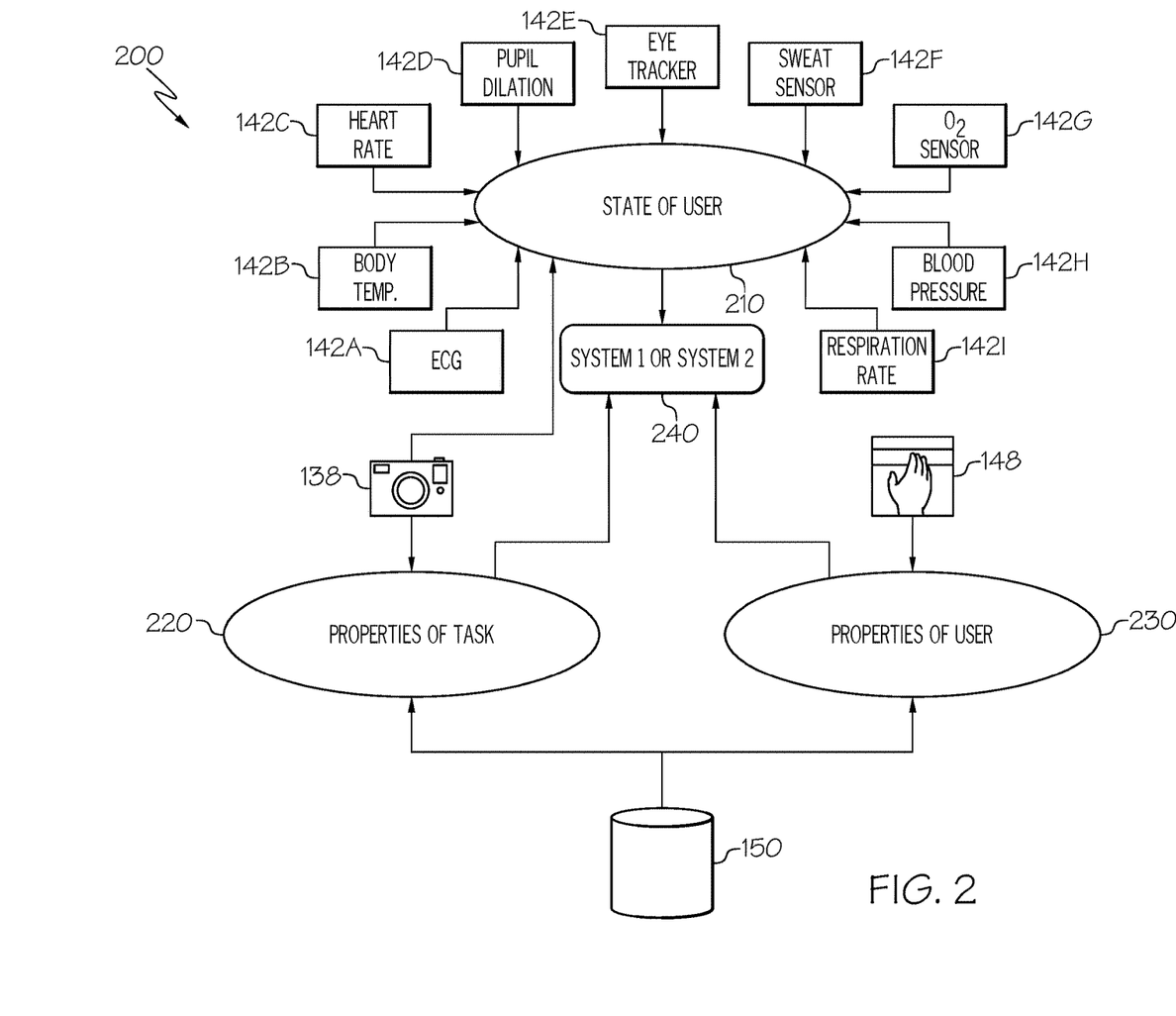
FIG. 2 depicts an information flow diagram for determining whether a user employs System 1 type thinking or System 2 type thinking when engaged in a task, according to one or more embodiments shown and described herein.

Turning now to FIG. 2, an information flow diagram 200 for determining whether a user employs System 1 type thinking or System 2 type thinking when engaged in a task is depicted. The information flow diagram 200 illustrates the sources of information that may be utilized by analysis modules 210-240 implemented by the electronic control unit 130. The system and method may be implemented using an electronic control unit 130 (FIG. 1) that includes one or more processors 132 (FIG. 1). The electronic control unit 130 receives information relating to the properties of the task, the properties of the user, and the state of the user. The electronic control unit 130 may be in communication with one or more input devices for providing information regarding the properties of the task, the properties of the user, and the state of the user.

The input device may be one or more sensors, such as a camera 138, one or more physiological sensors 142A-142I or another type of sensor that is able to provide information regarding the state of the user. For example, concerning the state of the user, the sensors may be able to detect the user stress level (e.g., based on rapid heartbeat, dilated pupils, rapid movement of the eyes, presence of sweat or the like), fatigue level (e.g., based on eye movement, presence of bags under eyes, or the like), state of health (e.g., based on body temperature, blood oxygen levels, heartbeat, blood pressure, or the like), and if the user is multitasking. FIG. 2 depicts a variety of types of physiological sensors 142A-142I. As a non-limiting example, the physiological sensors 142A-142I may include an electrocardiogram sensor 142A, a body temperature sensor 142B, a heart rate sensor 142C, a pupil dilation sensor 142D (e.g. implemented using the one or more cameras 138 and/or the eye-tracking system 140), an eye tracker 142E (e.g., an eye-tracking system 140), a sweat sensor 142F, an oxygen sensor 142G, a blood pressure sensors 142H, or a respiration rate sensor 142I. These are merely a few example physiological sensors 142A-142I that may be implemented in the system 100 to monitor various physiological conditions of the user. The physiological sensors 142A-142I may be coupled to a user through a wearable device 149 (FIG. 3), embedded in a seat or floor to monitor a user that is in contact with the seat or the floor, or configured to monitor the user from a distance when the user is within a detection range of the one or more physiological sensors 142A-142I. The physiological sensors 142A-142I generate electrical signals in response to the conditions each sensor is configured to monitor and transmit the electrical signals to the electronic control unit 130 for analysis.

In addition to sensors, the system 100 may also obtain information including one or more properties of the task and one or more properties of the user from a data storage component 150, an input device such as a display 148 that is touch enabled, an input device 136, one or more cameras 138 or the like. The electronic control unit 130 request and/or receive information pertaining to the one or more properties of one or more tasks. Such information may include the type of task that a user is currently engaged, the typical length it takes to complete the task, the number of steps involved with completing the task, what senses such as sight, hearing taste, or touch are involved with completing the task, whether the task involves the processing or words, written information, sounds, and/or images or the like.

Additionally, the system 100 obtains information about the user that is engaged in the task. For example, one or more properties of the one or more users 154 may include properties such as an experience level of the user performing the task, the number of times the user has completed the particular task or similar tasks in the past, the amount of time that the user previously engaged in solving the same or similar task, whether the user is proficient in a set of particular skills that correlate to the one or more properties of the task, the frequency in which a user interacts with the particular task and/or the like.

As depicted in FIG. 2, the electronic control unit 130 is configured with one or more analysis modules (e.g., a state of user module 210, a properties of task module 220, and a properties of user module 230) to analyze data from at least three particular categories (e.g., one or more properties of the task, one or more properties of the user, and the state of the user) to determine whether a user is or will use either System 1 type thinking or System 2 type thinking for the particular task. The electronic control unit 130 analyzes the physiological response data generated by the physiological sensors 142A-142I to determine the state of the user. The state of the user may be multifaceted. That is, in order to determine the effect a task is having on the user a base line state of the user may be needed. For example, someone in poor physical shape may have naturally have high blood pressure or a higher than normal heart rate which may not be indicative of the stress level of the user, but rather a result of their current health. Accordingly, the state of user module 210 employed by the electronic control unit 130 may be configured to determine a state of health of a user, which may then be used as a baseline in determining one or more characteristics of the user presenting themselves in response to engaging in a task. For example, these characteristics may include the stress level, fatigue level, or the like. Based on the determined state of the user based on the one or more physiological sensors 142A-142I configured to sense the one or more characteristics of the user, the electronic control unit 130 may determine whether the state of the user correlates to someone engaged in System 1 type thinking or System 2 type thinking. As a non-limiting example, generally, the more that a user is under stress, fatigue, or in a poor state of health, the more likely they are to engage in System 1 type thinking. Conversely, being calm, well rested, and in better health, the more likely the user is to engage in System 2 type thinking. A person who is multitasking is more likely to engage in System 1 type thinking. However, the state of the user is not independently indicative of the type of thinking the user is engaged in for a particular task.

As such, the electronic control unit 130 may also be in communication with one or more sensors (e.g., the one or more cameras 138 and/or an input device such as a display 148 that is touch enabled or an input device 136) configured to collect information regarding the properties of the user task and/or the properties of the user and/or one or more databases (e.g., a data storage component 150) that store information regarding the properties of the user task and/or the properties of the user. The electronic control unit 130 may be further configured with a properties of task module 220 that is implemented to analyze the one or more properties of the task to determine whether the task may be a task that is inherently one that a user would implement System 1 type thinking or System 2 type thinking to complete. That is, electronic control unit 130 may receive information pertaining to the particular task from a database storing information regarding the task. For example the one or more properties of the task may include the type of task, the typical length it takes to complete the task, the number of steps involved with completing the task, what senses (e.g., sight, hearing, taste, touch) are involved with completing the tasks, and/or if the task involves the processing of words/written information or sounds/images It is noted that the electronic control unit 130 may also include a process of determining what task the user is currently engaged in. In some embodiments, the electronic control unit 130 the determination as to what task the user is currently engaged in is merely a function of querying the operating state of the system to determine what functionality is currently being utilized. For example, in the context of a vehicle, the system 100 may implemented as part of the vehicle to user interface and the vehicle system currently active may be the navigation system. Therefore, the electronic control unit 130 may determine that the user is currently engaged in the navigation of the vehicle as opposed to communicating with another person via phone or multimedia messaging, if those systems are not currently active.

Referring back to the analysis of the one or more properties of the task to determine whether the task may be a task that is inherently one that a user would implement System 1 type thinking or System 2 type thinking to complete, the properties of task module 220 may be preconfigured with a plurality of guiding principles for making the determination or a prediction as to which type of thinking the user may be engaged in with respect to the particular task. As a non-limiting example, generally, tasks that have more steps, take longer to complete, and involve the processing of words/written information cause the user to engage in System 2 type thinking. Whereas, tasks that have fewer steps, can be completed quickly, and involve the processing of visual/audible information generally cause the user to engage in System 1 type thinking. These and other guiding principles for making the determination or a prediction as to which type of thinking the user may be engaged in with respect to the particular task may be predefined in the properties of task module 220 and implemented by the electronic control unit 130. As similarly stated with respect to the state of the user, the one or more properties of the task are not independently indicative of the type of thinking the user is engaged in for a particular task.

As such, the electronic control unit 130 may be further configured with a properties of user module 230 that is implemented to analyze the one or more properties of the user to determine whether the task may be a task that is inherently one that a user would implement System 1 type thinking or System 2 type thinking to complete. That is, electronic control unit 130 may request and receive information pertaining to the particular user from a database storing information regarding the user. The information may include properties such as experience level of the user performing the task, the number of times the user has completed the particular task or similar tasks in the past, the amount of time that the user previously engaged in solving the same or similar task, whether the user is proficient in a set of particular skills that correlate to the one or more properties of the task, the frequency in which a user interacts with the particular task and/or the like. As discussed hereinabove, the information may be defined in a user profile that is generated based on prior experiences a user has in completing a task and/or based on prompted feedback requested by the system of the user.

The properties of user module 230 provides guiding principles for the electronic control unit 130 to make a determination or at least a prediction as to what type of thinking a user may be engaged in in performing the particular task. As a non-limiting example, a user that is more experienced in solving a particular task is more likely to engage in System 1 type thinking, whereas a user with less experience is more likely to engage in System 2 type thinking when engaged with in the system task. Experience level may be defined by the number of times that the user has completed this particular task or task that is similar. In addition to experience level, the amount of time that the user previously required for solving the same or similar task may also be provided as well.

Once the information is generated and/or collected for each of the three factors (e.g., the properties of the task, the properties of the user, and the state of the user), electronic control unit 130 combines the determinations and/or predictions as to what type of thinking a user is currently engaged in based on analysis through each of the analysis modules 210-230. Since none of the factors are exclusively indicative of the type of thinking that the user employs when engaged in the particular task, the electronic control unit 130 implements another module 240 for weighing determinations and making a final determination and/or prediction as to whether the user is engaged in System 1 type thinking or System 2 type thinking. As discussed in more detail herein, the electronic control unit 130 unit may utilize one or more machine learning models trained in digesting the multidimensional information and making a determination and/or prediction as to whether the user is engaged in System 1 type thinking or System 2 type thinking for the particular task.

In some embodiments, the determination the electronic control unit 130 makes as an output after implementing each of the analysis modules 210-230 may be a determination having a confidence value. The confidence value indicates how likely, based on the information analyzed by that particular module, that a user is engaged in either System 1 type thinking or System 2 type thinking. The confidence value may be a percentage on a scale of 0% to 100% with 100% representing strength in the determination made in response to the analysis performed with the particular module.

Figure 3:
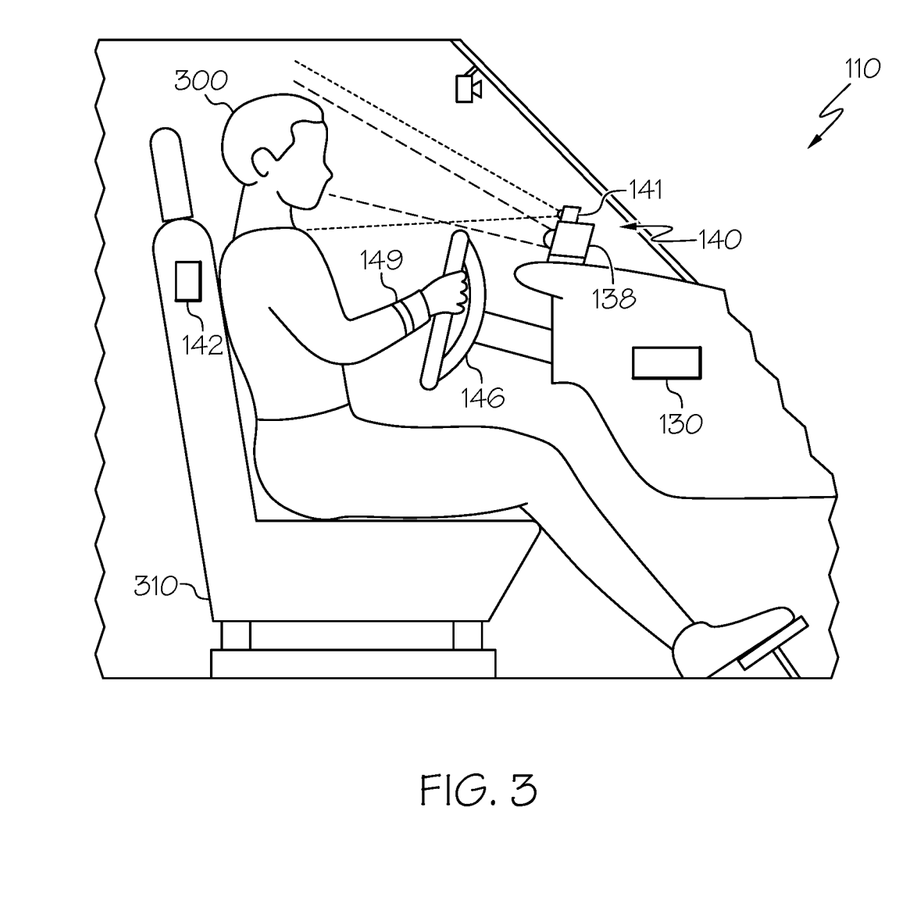
FIG. 3 depicts an example implementation of the system deployed in a vehicle for determining whether a user employs System 1 type thinking or System 2 type thinking when engaged in a vehicle based task, according to one or more embodiments shown and described herein.

Turning to FIG. 3, an example implementation of the system 100 deployed in a vehicle 110 for determining whether a user is relying on System 1 type thinking or System 2 type thinking when engaged in a vehicle based task is depicted. In some embodiments, physiological sensors 142 are deployed within a vehicle cabin to capture physiological response data of the user 300 (e.g., the driver) when she is engaged in various tasks. For example, as depicted an eye-tracking system 140 may be positioned in the vehicle 110 so that a camera or detection device (e.g., 138) is configured to capture eye movement, pupil dilation, head, and/or body positions of the driver or the like. In some embodiments, an illuminating device 141, for example, an infrared lamp, may direct infrared light toward the driver to enhance detection of eye movement, pupil dilation, head, and/or body positions. Furthermore, one or more physiological sensors 142 may be configured within the vehicle seat 310 to monitor characteristics of the user 300, such as, but not limited to respiration rate, heart rate, body temperature, or the like. In some embodiments, the one or more physiological sensors 142 may be implemented in a wearable device 149 that is communicatively coupled to the electronic control unit 130. The user may be engage in vehicle related tasks such as interacting with a navigation system to obtain directions to a destination, changing a playlist on the audio system, reviewing or updating a schedule for pick-ups, deliveries, or appointments, or other tasks. However, it is understood that implementation of the system 100 for determining whether a user employs System 1 type thinking or System 2 type thinking when engaged in a task in a vehicle 110 is merely one environment where the system 100 may be deployed.

Figure 4:
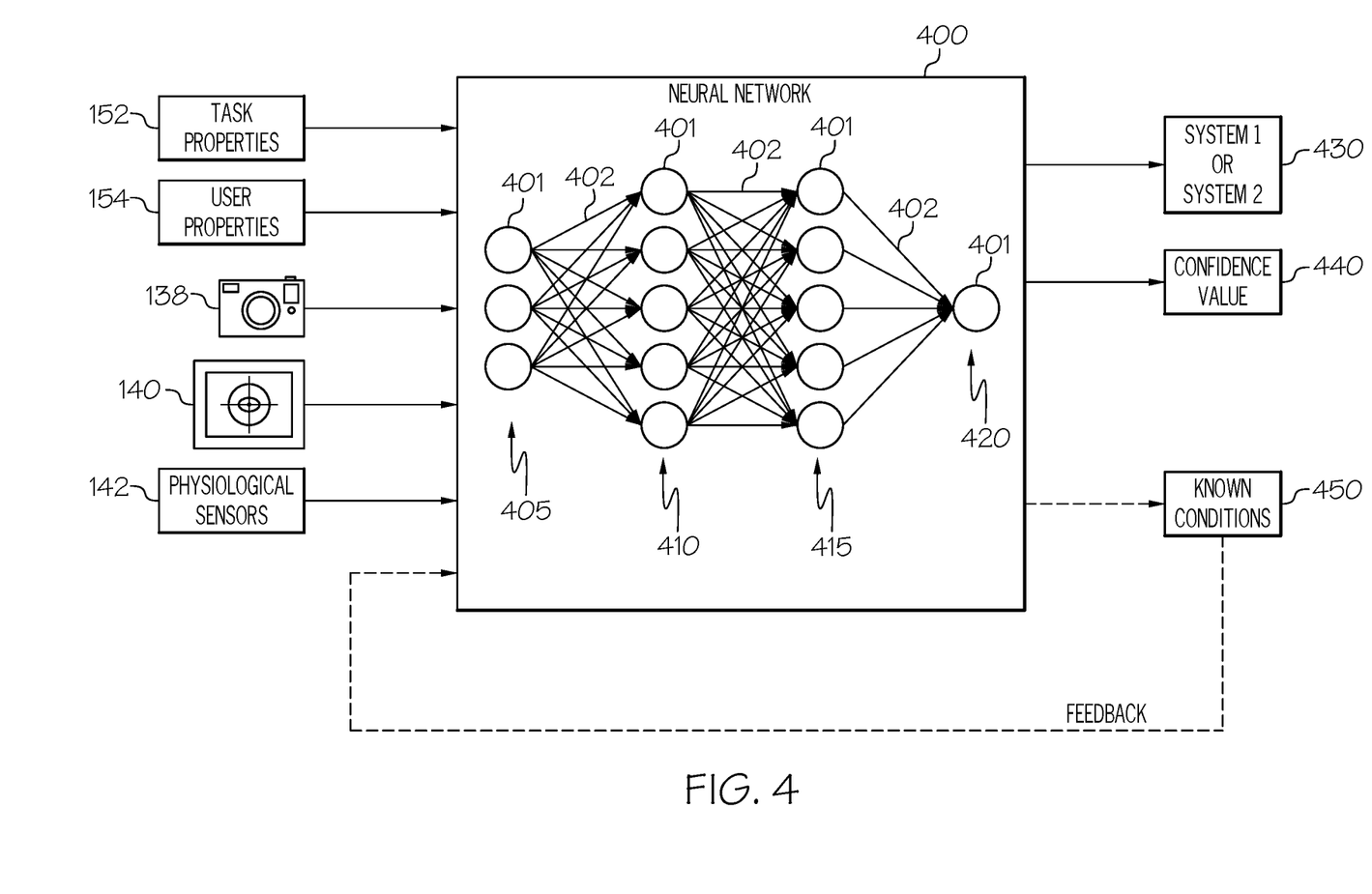
FIG. 4 depicts an illustrative diagram for a neural network model for predicting whether a user employs System 1 type thinking or System 2 type thinking when engaged in a task, according to one or more embodiments shown and described herein.

Referring now to FIG. 4, an illustrative diagram for a machine learning model such as a neural network 400 for predicting whether a user employs System 1 type thinking or System 2 type thinking when engaged in a task is depicted. In particular, FIG. 4 depicts a neural network 400 type machine learning model. However, it should be understood that various types of machine learning models may be implemented by the electronic control unit 130 for predicting or determining whether a user employs System 1 type thinking or System 2 type thinking when engaged in a task. As used herein, the term "machine learning model" refers to one or more mathematical models configured to find patterns in data and apply the determined pattern to new data sets to form a prediction. Different approaches, also referred to as categories of machine learning, are implemented depending on the nature of the problem to be solved and the type and volume of data. Categories of machine learning models include, for example, supervised learning, unsupervised learning, reinforcement learning, deep learning or a combination thereof.

Referring to a neural network 400 type machine learning model, for example, the neural network 400 may include one or more layers 405, 410, 415, 420, having one or more nodes 401, connected by node connections 402. The one or more layers 405, 410, 415, 420 may include an input layer 405, one or more hidden layers 410, 415, and an output layer 420. The input layer 405 represents the raw information that is fed into the neural network 400. For example, one or more properties of one or more tasks 152, one or more properties of one or more users 154, sensor data from the one or more cameras 138, the eye-tracking system 140, and/or the physiological response data from one or more physiological sensors 142 may be input into the neural network 400 at the input layer 405. The neural network 400 processes the raw information received at the input layer 405 through nodes 401 and node connections 402. The one or more hidden layers 410, 415, depending on the inputs from the input layer 405 and the weights on the node connections 402, carry out computational activities. In other words, the hidden layers 410, 415 perform computations and transfer information from the input layer 405 to the output layer 420 through their associated nodes 401 and node connections 402.

In general, when a neural network 400 is learning, the neural network 400 is identifying and determining patterns within the raw information received at the input layer 405. In response, one or more parameters, for example, weights associated to node connections 402 between nodes 401, may be adjusted through a process known as back-propagation. It should be understood that there are various processes in which learning may occur, however, two general learning processes include associative mapping and regularity detection. Associative mapping refers to a learning process where a neural network 400 learns to produce a particular pattern on the set of inputs whenever another particular pattern is applied on the set of inputs. Regularity detection refers to a learning process where the neural network 400 learns to respond to particular properties of the input patterns. Whereas in associative mapping the neural network 400 stores the relationships among patterns, in regularity detection the response of each unit has a particular "meaning". This type of learning mechanism may be used for feature discovery and knowledge representation.

Neural networks possess knowledge that is contained in the values of the node connection weights. Modifying the knowledge stored in the network as a function of experience implies a learning rule for changing the values of the weights. Information is stored in a weight matrix W of a neural network 400. Learning is the determination of the weights. Following the way learning is performed, two major categories of neural networks can be distinguished: 1) fixed networks in which the weights cannot be changed (i.e., dW/dt=0) and 2) adaptive networks that are able to change their weights (i.e., dW/dt not=0). In fixed networks, the weights are fixed a priori according to the problem to solve.

In order to train a neural network 400 to perform some task, adjustments to the weights are made in such a way that the error between the desired output and the actual output is reduced. This process may require that the neural network 400 compute the error derivative of the weights (EW). In other words, it must calculate how the error changes as each weight is increased or decreased slightly. A back propagation algorithm is one method that is used for determining the EW.

The algorithm computes each EW by first computing the error derivative (EA), the rate at which the error changes as the activity level of a unit is changed. For output units, the EA is simply the difference between the actual and the desired output. To compute the EA for a hidden unit in the layer just before the output layer, first all the weights between that hidden unit and the output units to which it is connected are identified. Then, those weights are multiplied by the EAs of those output units and the products are added. This sum equals the EA for the chosen hidden unit. After calculating all the EAs in the hidden layer just before the output layer, in like fashion, the EAs for other layers may be computed, moving from layer to layer in a direction opposite to the way activities propagate through the neural network 400, hence "back propagation". Once the EA has been computed for a unit, it is straightforward to compute the EW for each incoming connection of the unit. The EW is the product of the EA and the activity through the incoming connection. It should be understood that this is only one method in which a neural network 400 is trained to perform a task.

Still referring to FIG. 4, the neural network 400 may include one or more hidden layers 410, 415 that feed into one or more nodes 401 of an output layer 420. There may be one or more output layers 420 depending on the particular output the neural network 400 is configured to generate. For example, the neural network 400 may be trained to output a prediction 430 as to whether a user is engaged in System 1 type thinking or System 2 type thinking when performing a particular task. Additionally, the neural network 400 may also generate a confidence value 440 indicative of how likely the user is employing System 1 type thinking or System 2 type thinking. Moreover, the known conditions 450 may be determined by the neural network 400 in training and used as feedback for further training the neural network 400.

Figure 5:
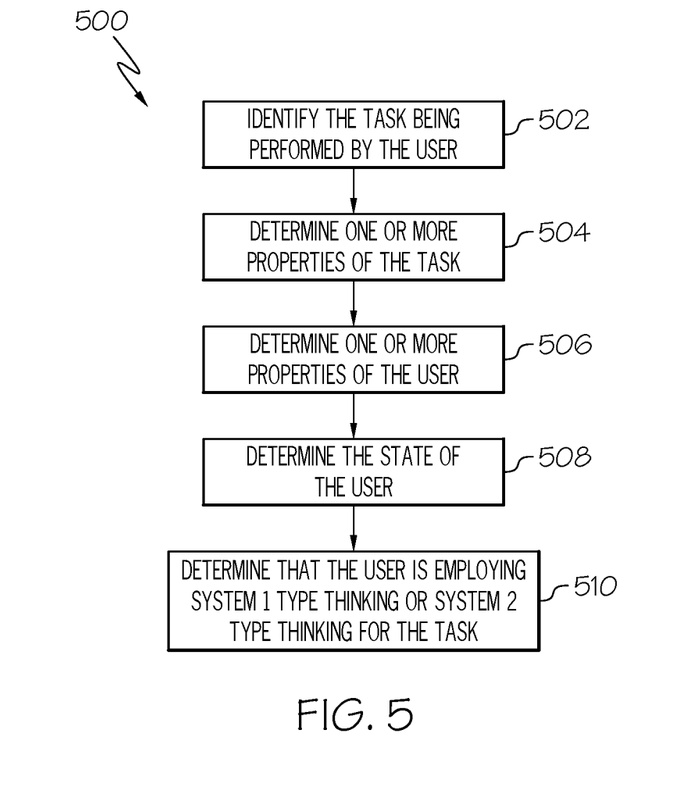
FIG. 5 depicts an illustrative flow diagram for determining whether a user employs System 1 type thinking or System 2 type thinking when engaged in a task, according to one or more embodiments shown and described herein.

Turning to FIG. 5 an illustrative flow diagram 500 for determining whether a user employs System 1 type thinking or System 2 type thinking when engaged in a task is depicted. In other words, the flow diagram 500 illustrates an example method implemented by the electronic control unit 130 to determine or at least predict whether the user is engaged in System 1 type thinking or System 2 type thinking when completing a particular task. Flow diagram 500 is only one method, implemented by a system for determining or at least predicting whether the user is engaged in System 1 type thinking or System 2 type thinking when completing a particular task. Other methods that embody the analysis of the three factors (e.g., the state of the user, properties of the task, and properties of the user) as described herein may be implemented without departing from the scope of the present disclosure.

At block 502, the electronic control unit 130 identifies the task that is being performed by the user. As discussed hereinabove, the determination may be made based on the current operation of the system interacting with the user, such as operation of a navigation system by a user 300 (e.g., the driver) of a vehicle 110. In some embodiments, however, image data collected by the one or more cameras 138 may be analyzed to determine what task the user is preforming. For example, the one or more cameras 138 may identify the task of cooking through image data that captures the user interacting with cooking utensils, mixing bowls, or the like. Additionally, at block 502 the electronic control unit 130 may obtain through image data information as to whether the user is multitasking or focusing on a particular task.

At block 504, the electronic control unit 130 may query a database (e.g., a data storage component 150) having one or more properties of one or more tasks 152 for properties pertaining to the identified task (e.g., the particular task the user is engaged). As a result, the electronic control unit 130 determines one or more properties for the identified task based on information received from the database. In some embodiments, at block 504 the electronic control unit 130 may further analyze the one or more properties for the identified task to determine whether, based on the one or more properties, the task is one that a user may engage System 1 type thinking or System 2 type thinking as described, for example, with reference to the properties of task module 220.

At block 506, the electronic control unit 130 may query a database (e.g., a data storage component 150) having one or more properties of one or more users 154 for properties pertaining to the user performing the identified task. As a result, the electronic control unit 130 determines one or more properties for the user based on information received from the database. These properties may relate to a user's expertise or experience in engaging with and/or completing a particular task. In some embodiments, at block 506 the electronic control unit 130 may further analyze the one or more properties of the user to determine whether, based on the one or more properties, the user is likely engaging System 1 type thinking or System 2 type thinking to complete the task as described, for example, with reference to the properties of user module 230.

At block 508, the electronic control unit 130 receives one or more signals from the one or more sensors for example, including the one or more cameras 138, the eye-tracking system 140, the physiological sensors 142, or the like. The electronic control unit 130 analyzes the signals, which may include physiological response data for a user who is engaged in performing the identified task. Determinations as to the stress level, fatigue level, and the like are made through analysis of the one or more signals from the one or more sensors by the electronic control unit 130. Through analysis of the one or more physiological sensors 142 configured to sense one or more characteristics of the user, the electronic control unit 130 determines the state of the user. In some embodiments, at block 508 the electronic control unit 130 determines, based on the state of the user, whether the user is engaging System 1 type thinking or System 2 type thinking to complete the task as described, for example, with reference to the properties of user module 230.

At block 510, the electronic control unit 130 compiles the determinations made through the analyses performed at blocks 504-508 and makes a determination or at least a prediction with a level of confidence as to whether a user employs System 1 type thinking or System 2 type thinking when engaged in the task. The determination may be made by weighting the three factors (e.g., the determined one or more properties of the task, the determined one or more properties of the user, and the determined state of the user). In some embodiments, the electronic control unit 130 may weigh one factor more than another based on a confidence level determined for that factor. That is, if one factor is more conclusively indicative of System 1 type thinking or System 2 type thinking, then that factor is weighted more when combining all three factors in making the determination that a user is employing System 1 type thinking or System 2 type thinking when engaged in the task.

The functional blocks and/or flowchart elements described herein may be translated onto machine-readable instructions. As non-limiting examples, the machine-readable instructions may be written using any programming protocol, such as: (i) descriptive text to be parsed (e.g., such as hypertext markup language, extensible markup language, etc.), (ii) assembly language, (iii) object code generated from source code by a compiler, (iv) source code written using syntax from any suitable programming language for execution by an interpreter, (v) source code for compilation and execution by a just-in-time compiler, etc. Alternatively, the machine-readable instructions may be written in a hardware description language (HDL), such as logic implemented via either a field programmable gate array (FPGA) configuration or an application-specific integrated circuit (ASIC), or their equivalents. Accordingly, the functionality described herein may be implemented in any conventional computer programming language, as pre-programmed hardware elements, or as a combination of hardware and software components.

It should be understood that the embodiments described herein are directed to systems and methods for determining whether a user employs System 1 type thinking or System 2 type thinking when engaged in a task based on three factors. In some embodiments, the systems and methods may utilize an electronic control unit and/or neural network to receive, analyze, and make a determination or prediction as to whether a user is engaging System 1 type thinking or System 2 type thinking in performing a particular task. For example, a method for determining whether a user employs System 1 type thinking or System 2 type thinking when engaged in a task may include determining one or more properties of the task based on information regarding the task received from a database storing information regarding the task, determining one or more properties of the user with respect to the task, determining a state of the user based on one or more physiological sensors configured to sense one or more characteristics of the user, and determining that the user employs System 1 type thinking or System 2 type thinking when engaged in the task based on the determined one or more properties of the task, the determined one or more properties of the user, and the determined state of the user.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for determining whether a user employs System 1 type thinking or System 2 type thinking when engaged in a task deployed by a system of a vehicle, the method comprising:
   determining one or more properties of the task based on information regarding the task received from a database storing information regarding the task;
   determining one or more properties of the user with respect to the task;
   determining a state of the user based on one or more physiological sensors configured to sense one or more characteristics of the user;
   determining that the user employs System 1 type thinking or System 2 type thinking when engaged in the task based on the determined one or more properties of the task, the determined one or more properties of the user, and the determined state of the user; and
   adapting the system of the vehicle deploying the task the user is engaged in performing, wherein the system of the vehicle is adapted to interact with the user based on a type of thinking the user is determined to employ while engaged in the task.

2. The method of claim 1, wherein the state of the user includes at least one of a stress level, a fatigue level, or a state of health of the user.

3. The method of claim 2, wherein the stress level is defined by at least one of a heart rate, a pupil dilation, an eye movement, or a perspiration of the user.

4. The method of claim 3, wherein an elevated level of stress is indicative of the user employing System 1 type thinking for the task.

5. The method of claim 2, wherein the fatigue level is defined by at least one of an eye movement or discoloration of or around eyes of the user.

6. The method of claim 2, wherein an elevated level of fatigue is indicative of the user employing System 1 type thinking for the task.

7. The method of claim 1, wherein the one or more properties of the user includes a level of experience of the user with the task.

8. The method of claim 7, wherein when the user is determined to have a high level of experience with the task, the state of the user is indicative of the user employing System 1 type thinking for the task.

9. The method of claim 7, wherein the user is determined to employ System 1 type thinking when the one or more properties of the task indicates the task involves at least one of visual information, audible information, or a limited number of steps.

10. A system for determining whether a user employs System 1 type thinking or System 2 type thinking when engaged in a task deployed by a system of a vehicle, the system comprising:
    one or more physiological sensors configured to sense one or more characteristics of the user; and
    an electronic control unit communicatively coupled to the one or more physiological sensors, the electronic control unit configured to:
      determine one or more properties of the task based on information regarding the task received from a database storing information regarding the task,
      determine one or more properties of the user with respect to the task,
      determine a state of the user based on the one or more characteristics of the user sensed by the one or more physiological sensors,
      determine that the user employs System 1 type thinking or System 2 type thinking when engaged in the task based on the determined one or more properties of the task, the determined one or more properties of the user, and the determined state of the user; and
      adapt the system of the vehicle deploying the task the user is engaged in performing, wherein the system of the vehicle is adapted to interact with the user based on a type of thinking the user is determined to employ while engaged in the task.

11. The system of claim 10, wherein the state of the user includes at least one of a stress level, a fatigue level, or a state of health of the user.

12. The system of claim 11, wherein the stress level is defined by at least one of a heart rate, a pupil dilation, an eye movement, or a perspiration of the user.

13. The system of claim 12, wherein an elevated level of stress is indicative of the user employing System 1 type thinking for the task.

14. The system of claim 11, wherein the fatigue level is defined by at least one of an eye movement or discoloration of or around eyes of the user.

15. The system of claim 11, wherein an elevated level of fatigue is indicative of the user employing System 1 type thinking for the task.

16. The system of claim 10, wherein the one or more properties of the user includes a level of experience of the user with the task.

17. The system of claim 16, wherein the user is determined to employ System 1 type thinking when the user is determined to have a high level of experience with the task, the state of the user.

18. The system of claim 10, wherein the one or more physiological sensors includes at least one of a heart rate sensor, a pupil dilation sensor, a sweat sensor, an eye tracker, a blood pressure sensor, a respiration rate sensor, a body temperature sensor, or an electrocardiogram.

* * * * *

UNITED STATES PATENT AND TRADEMARK OFFICE
CERTIFICATE OF CORRECTION

| | | |
|---|---|---|
| PATENT NO. | : 11,864,897 B2 | Page 1 of 1 |
| APPLICATION NO. | : 17/227671 | |
| DATED | : January 9, 2024 | |
| INVENTOR(S) | : Rumen Iliev et al. | |

It is certified that error appears in the above-identified patent and that said Letters Patent is hereby corrected as shown below:

In the Specification

In Column 10, Line(s) 24, after "may", delete "have".

In Column 11, Line(s) 11, after "may", insert --be--.

In Column 15, Line(s) 11, delete "preforming" and insert --performing--, therefor.

Signed and Sealed this
Eleventh Day of March, 2025

Coke Morgan Stewart
*Acting Director of the United States Patent and Trademark Office*